United States Patent
Nusse (10) Patent No.: US 10,617,882 B2
(45) Date of Patent: Apr. 14, 2020

(54) ELECTRICAL BODY STIMULATOR CUSHION DEVICE, A MEDICAL OR THERAPEUTIC DEVICE COMPRISING SAME

(71) Applicants: Louis Biesbrouck, Diemen (NL); Robert Nusse, Heerhugowaard (NL)

(72) Inventor: Robert Nusse, Heerhugowaard (NL)

(73) Assignees: Louis Biesbrouck, Diemen (NL); Robert Nusse, Heerhugowaard (NL)

( * ) Notice: Subject to any disclaimer, the term of this patent is extended or adjusted under 35 U.S.C. 154(b) by 240 days.

(21) Appl. No.: 15/553,957

(22) PCT Filed: Feb. 24, 2016

(86) PCT No.: PCT/NL2016/050131
§ 371 (c)(1),
(2) Date: Aug. 25, 2017

(87) PCT Pub. No.: WO2016/137319
PCT Pub. Date: Sep. 1, 2016

(65) Prior Publication Data
US 2018/0036548 A1    Feb. 8, 2018

(30) Foreign Application Priority Data

Feb. 26, 2015   (NL) ..................... 2014356

(51) Int. Cl.
*A61N 5/06*   (2006.01)
*A61N 2/00*   (2006.01)
(Continued)

(52) U.S. Cl.
CPC ......... *A61N 2/002* (2013.01); *A61N 1/36014* (2013.01); *A61N 2/004* (2013.01);
(Continued)

(58) Field of Classification Search
CPC . A61N 1/22; A61N 2/00; A61N 2/002; A61N 2/004; A61N 2/02; A61N 2005/0658; A61N 2005/0659; A61N 2005/066
(Continued)

(56) References Cited

U.S. PATENT DOCUMENTS 4,825,868 A *  5/1989  Susa ................. A61N 5/06
                                                  219/217
9,005,101 B1 *  4/2015  Van Erlach ...... A61B 17/22004
                                                  600/9
(Continued)

FOREIGN PATENT DOCUMENTS

WO       98/25667 A1    6/1998
WO    2014/084729 A1    6/2014

OTHER PUBLICATIONS

International Search Report for PCT/NL2016/050131 filed on Feb. 24, 2016 in the name of Louis Biesbrouck. dated Jun. 14, 2016. 6 pages.

(Continued)

*Primary Examiner* — Samuel G Gilbert
(74) *Attorney, Agent, or Firm* — Steinfl + Bruno LLP (57) ABSTRACT

An electrical body stimulator cushion device, use thereof and a medical or therapeutic device which includes a body stimulator cushion device made from a layer of pliable material, an electrical body stimulator having a plurality of interconnected electrical conductors, a top and a bottom isolating layer between which the electrical conductors are located, and an infrared reflector foil, located between the layer of pliable material and the electrical body stimulator. When the electrical body stimulator cushion device is connected to a grounded power supply, the plurality of electrical conductors of the electrical body stimulator are arranged to emit infrared radiation towards a user body, generate a magnetic field, and provide a current pathway for directing (Continued)

a body stimulating current from the plurality of electrical conductors via the body to ground.

17 Claims, 4 Drawing Sheets

(51) Int. Cl.
*A61N 2/02* (2006.01)
*A61N 1/36* (2006.01)

(52) U.S. Cl.
CPC ............... *A61N 2/02* (2013.01); *A61N 5/06* (2013.01); *A61N 2005/066* (2013.01); *A61N 2005/0638* (2013.01); *A61N 2005/0645* (2013.01); *A61N 2005/0659* (2013.01); *A61N 2005/0666* (2013.01)

(58) Field of Classification Search
USPC .......................................... 600/9–15; 607/100
See application file for complete search history.

(56) References Cited

U.S. PATENT DOCUMENTS

| | | |
|---|---|---|
| 2012/0122636 A1 | 5/2012 | Shurtleff |
| 2012/0191164 A1 | 7/2012 | Gander et al. |
| 2014/0215708 A1 | 8/2014 | Benda et al. |
| 2018/0116421 A1* | 5/2018 | Goncalves ........... A47C 27/088 |

OTHER PUBLICATIONS

Written Opinion for PCT/NL2016/050131 filed on Feb. 24, 2016 in the name of Louis Biesbrouck. dated Jun. 14, 2016. 8 pages.

\* cited by examiner

ELECTRICAL BODY STIMULATOR CUSHION DEVICE, A MEDICAL OR THERAPEUTIC DEVICE COMPRISING SAME

CROSS-REFERENCE TO RELATED APPLICATIONS

The present application is the U.S. National Stage of International Patent Application No. PCT/NL2016/050131 filed on Feb. 24, 2016 which, in turn, claims priority to Dutch (NL) Patent Application No. 2014356 filed on Feb. 26, 2015.

TECHNICAL FIELD

The invention generally relates to an electrical body stimulator cushion device for stimulating the body of an individual, a medical or therapeutic device comprising such electrical body stimulator device, and to the use of such a device in medical or therapeutic equipment or in wellness therapy, natural health care, physiotherapy, thermotherapy, heat therapy, electromagnetic therapy, and/or electrotherapy.

BACKGROUND OF THE INVENTION

In wellness therapy various methods are known for treating the body of an individual, i.e. a human being or animal, by stimulating the body via heat, magnetic fields, or electrical currents. Specifically, infrared radiation devices for stimulating the body are known from the state of the art, for example in the form of infrared lights. Infrared, IR, radiation is a type of electromagnetic radiation with longer wavelengths than those of visible light, ranging from the red coloured end of the visible spectrum at about 740 nanometres, nm, to about 1000 micrometres, μm. Infrared radiation is gaining popularity as a heat therapy method of natural health care and physiotherapy.

The state of the art further comprises magnetic field body stimulating devices, wherein the application of a magnetic field to the body of an individual is deemed beneficial to his or her health. These devices are applied in electromagnetic therapy for stimulating the body and/or treating deceases of the human or animal body.

Furthermore devices for providing a body stimulating current through a body are known from the state of the art. For example, in electrotherapy a, preferably alternating, current runs through parts of the body for relaxation of muscle spasms, prevention and retardation of disuse atrophy, increase of local blood circulation, etc.

The main drawback of the state of the art devices is that their application is cumbersome to the subject. The state of the art devices are often uncomfortable, costly, large, difficult to transport, require specific training instructions, or require the user to be fixed in a certain position for a lengthy period of time, resulting in a limited applicability of the state of the art devices.

SUMMARY

It is an object of the present invention to provide a versatile electrical body stimulator cushion device, preferably one which can be easily applied to the body of an individual without substantial intrusion upon his or her daily life.

In a first aspect there is provided an electrical body stimulator cushion device comprising a layer of pliable material. The device further comprises a flexible electrical body stimulator comprising a plurality of interconnected electrical conductors arranged substantially parallel to one another and a top and a bottom isolating layer between which the plurality of electrical conductors are located. Furthermore, the device comprises an infrared reflector foil, located between the layer of pliable material and the electrical body stimulator, such that the bottom isolating layer of the electrical body stimulator is facing the infrared reflector foil.

When the electrical body stimulator cushion device is powered, the plurality of electrical conductors of the electrical body stimulator emit infrared radiation towards the body of a user, when located adjacent, i.e. against or close to the electrical body stimulator cushion device, to generate a magnetic field at a distance from the electrical body stimulator cushion device towards the body of the user, and when the electrical conductors of the electrical body stimulator are connected to a grounded mains power supply and the body of the user is in electrical contact with the electrical body stimulator cushion device to provide a current pathway for directing a body stimulating current from the plurality of electrical conductors via the body of a user to ground or earth. The layers of the body stimulator cushion device are dimensioned to provide an effective electrical resistance of the current pathway such that a maximum body stimulating current is limited to a non-hazardous current range.

The invention is based on the insight to provide an easy to use and versatile therapeutic device by combining the infrared radiation, magnetic field, and body stimulating current effects in a single device. The device according to the present invention combines the beneficial effects of the infrared radiation, magnetic field, and body stimulating current and is widely applicable in various treatment methods. From the state of the art, separate devices are known for stimulating the body via infrared radiation, or via magnetic fields, or via body stimulating currents, but the device according to the present invention distinguishes itself from the prior art by providing a single device which combines the infrared radiation, magnetic field, and body stimulating current for simultaneous stimulation of a body, advantageously eliminating the need for separate devices.

The invention is further based on the insight that through the flexibility and pliability of the layers and foil, the electrical body stimulator cushion device becomes comfortable and easily applicable. Since the device is pliable and flexible, it can be easily applied to any part of the user's body in a comfortable manner. The user can sit or lie on the device or the device can be folded against or wrapped around parts of the body, such as an arm or leg, allowing easy application of the device. Due to its layered and preferably planar structure, the cushion device can be easily applied, for example, in a chair or bed for comfort and non-intrusive integration into the user's daily life. The device according to the present invention can thus be applied in a wide spectrum of wellness therapies, resulting in a versatile therapeutic or medical treatment device.

In an embodiment of the invention, the infrared reflector foil is an electrically isolating foil. In another embodiment of the invention the infrared reflector foil is a heat reflector foil. A foil has the advantageous property that it is deformable such that the electrical body stimulator cushion device can easily be held in good and tight mechanical contact to the body of a user. The electrically isolating foil is preferably substantially reflective for infrared radiation emitted in the Far Infrared Region, FIR, in particular for infrared radiation emitted in a range of 6000-14000 nm. The foil reflects most of the infrared radiation generated in its direction and towards the body of a user which is to be positioned adjacent the top isolating layer. This has the advantage that mainly all of the emitted energy, i.e. the infrared radiation, is focussed in the direction of the user's body, thereby maintaining a high efficiency standard. In another embodiment of the invention the infrared reflector foil is a heat reflector foil designed to reflect heat from the plurality of electrical conductors towards the body of a user positioned adjacent the top isolating layer.

In an embodiment of the invention the infrared reflector foil and the electrical body stimulator are arranged to direct the infrared radiation, and the magnetic field and/or the body stimulating current towards the body of the user which is to be positioned adjacent the top isolating layer. With a planar or substantially planar electrical body stimulator, the interconnected spaced apart electrical conductors provide for an efficient use of the available surface of the device in terms of infrared radiation, magnetic fields, and body stimulating currents, as the inventors realized that multiple conductors may be used as long as they are electrically isolated, i.e. spaced apart. For safety reasons, the plurality of electrical conductors are electrically shielded at both sides by the top and bottom isolating layers. This has the beneficial effect that electrical hazards are prevented as the electrical conductors can not be touched by a user.

For an easy electric coupling of the electrical body stimulator, in an embodiment of the invention, the electrical body stimulator cushion device comprises first and second power lines for powering the plurality of electrical conductors and connections means for electrically connecting the power lines to the electrical body stimulator.

In an embodiment of the invention the electrical power lines are integrated into the electrical body stimulator which has the beneficial effect that the power dissipated in the power lines contributes to the production of at least infrared radiation. Suitable electrical connecting means, such as a mating plug and socket type connectors, are well known to those skilled in the art of electrical engineering.

In an embodiment of the invention the effective electrical resistance of the current pathway of the body stimulating current is such that the maximum body stimulating current is limited to a non-hazardous range including currents less than 30 mA. Currents larger than 30 mA are generally deemed hazardous to the human body. The effective electrical resistance is made up, i.e. is a summation of, the electrical resistances of the individual layers of the electrical body stimulator arranged between the outer side of the electrical body stimulator cushion device, to be contacted by the body of a user, and the electrical conductors of the electrical body stimulator.

In an embodiment, the effective electrical resistance of the electrical body stimulator is such that the body stimulating current is unable to exceed 5 mA. Specifically the thickness of the top isolating layer is adjusted so that the amount of body stimulating current provided to the body of a user in contact with the electrical body stimulator and positioned adjacent the top isolating layer is within a desired safe range. This has further the advantage that the electrical body stimulating device can be produced adjusted to a user's body type.

In an embodiment of the invention, the top and bottom isolating layers are connected for forming a substantially isolating cover surrounding the plurality of electrical conductors. The cover protects the plurality of electrical conductors from contact with for example ambient moisture, thus further safeguards the user.

In an embodiment of the invention the plurality of electrical conductors are encased in a substantially insulating layer. This insulating layer is preferably produced from flexible, for example bendable, material. The advantage of this example is, among others, that the electrical body stimulator does not need to be produced according to a predetermined shape. The shape of the electrical body stimulator cushion device may be altered during placement, i.e. installation of the device, due to its flexibility. Suitable materials are, for example, electrically isolating soft plastics for the top and bottom isolating layers and the insulating layer. The insulating layer can be an adhesive. Also the thickness of the insulating layer can be added to adjust the amount of body stimulating current flowing through the body of a user.

In an embodiment of the invention the electrical body stimulator cushion device further comprises a cushion cover partially or completely surrounding the layer of pliable material, the electrical body stimulator and the infrared reflector foil. The cushion cover can be formed of any type of pliable and preferably soft material, such as gore-tex, air-tex, cotton, polyester or acryl. The cushion cover adds added comfort to the user when applying the electrical body stimulator cushion device.

Preferably, the electrical body stimulator cushion device further comprises an electric power control for controlling the power applied to the electrical body stimulator for emitting infrared radiation in the Far Infrared Region, in particular for emitting infrared radiation having a wavelength in a range of 6000-14000 nm. The inventors realized that the wavelength of the infrared radiation emitted by the electrical body stimulator is dependent on the electric power applied to the plurality of electrical conductors. By adjusting the power, the radiated infrared spectrum, i.e. the wavelengths of the generated radiation, are controlled. In a similar manner the magnetic field and/or body stimulating current can be controlled.

In an embodiment of the invention the plurality of interconnected electrical conductors form a plurality of substantially rectangular loops. The loop size and density can be varied to bring the emissions of the electrical body stimulator device, in particular the generated magnetic field, into conformity with the therapeutic or treatment needs of a user.

In an embodiment of the invention the electrical body stimulator cushion device is substantially cushion-shaped, wherein preferably the height or thickness of the device, measured along the stacking direction of the layers of the device, is small compared to a cross-section of the device, measured in a direction parallel to the plane of the layers. Thus a flexible electrical body stimulator cushion device is obtained which can easily be applied to a user's body. With a substantially planar electrical body stimulator cushion device, such that its thickness is small compared to its length and width, it does not obstruct the user during use. The planar cushion-shaped configuration also allows for easy integration of the device in for example a bed or chair, allowing a user to undergo lengthy treatments with the device in a comfortable manner.

The invention further relates to the a medical or therapeutic device comprising the electrical body stimulator cushion device according to the present invention in a medical or therapeutic device, such as a medical or therapeutic chair, bench, bed, table, matrass, or brace as well as the use thereof in medical or therapeutic treatment. As explained above, the device can be easily integrated into such medical or therapeutic devices. The invention also relates to the use of the electrical body stimulator cushion device according to the present invention in wellness therapy, natural health care, physiotherapy, thermotherapy, heat therapy, electromagnetic therapy, and/or electrotherapy.

The invention will now be explained in more detail with reference to the appended figures, which merely serve by way of illustration of the invention and which may not be construed as being limitative thereto.

DETAILED DESCRIPTION

Figure 1:
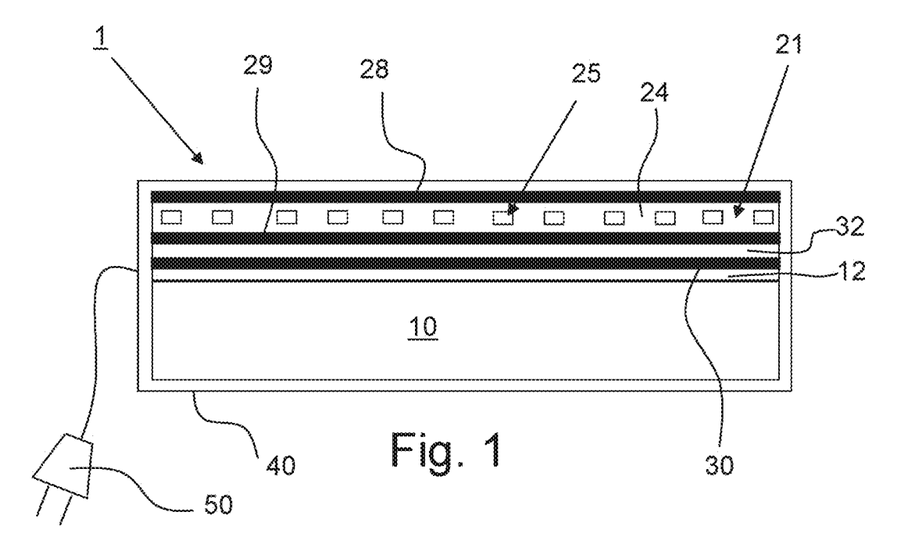
FIG. 1 shows, in a schematic form, not to scale, a cross sectional view of an example of an electrical body stimulator cushion device according to the invention.

FIG. 1 shows, in a schematic form, not to scale, a cross sectional view of an example of an electrical body stimulator cushion device 1 according to the invention.

The electrical body stimulator cushion device 1 according to the invention as shown in the example of FIG. 1, comprises a layer of pliable material 10 and a planar and flexible electrical body stimulator 21. The electrical body stimulator 21 comprises a plurality of interconnected electrical conductors 25 arranged substantially parallel to one another and a top electrically isolating layer 28 and a bottom electrically isolating layer 29 between which the plurality of electrical conductors 25 are located. An infrared reflector foil 30 is located between the layer of pliable material 10 and the electrical body stimulator 21, such that the bottom isolating layer 29 of the electrical body stimulator 21 is facing the infrared reflector foil 30. The infrared reflector foil 30 is connected on one side to the bottom isolating layer 29 via a first adhesive layer 32 and on the other side to the layer of pliable material 10 via a second adhesive layer 12.

The layer of pliable material 10 is preferably formed of a soft material for increasing the user's comfort. Furthermore the layer of pliable material 10 can have isolating properties to prevent heat or radiation to diffuse through the layer 10 away from the body of a user. Common materials for application in cushions can be used for forming the layer of pliable material 10, for example woven materials, wool, cotton, polyester or polyether.

The infrared reflector foil 30 is preferably an electrically isolating foil. Preferably an electrically isolating foil 30 is used which is substantially reflective for infrared radiation emitted in the Far Infrared Region, in particular for infrared radiation emitted in a range of 6000-14000 nm. Specifically, the infrared reflector foil 30 comprises a high grade plastic foil the surfaces of which have been ennobled similar to, for example, a thermos flask. Such a foil is commercially available from the TONZON company (called TONZON "folie"), and is applied in for example their products TONZON "Thermoskussens" and "Thermosheets" as were commercially available from TONZON in February 2015. Alternatively, an aluminium or PVC foil can be used.

The infrared reflector foil 30 is connected to the layer of pliable material 10 via an adhesive layer 12 and to the bottom isolating layer 29 of the electrical stimulator device 21 via an adhesive layer 32. Any type of adhesive known to the skilled person can be applied, such as glue. Preferably the adhesive layers 12 and 32 are electrically isolating.

The electrical body stimulator 21 comprises a bottom isolating layer 29 of electrically isolating material such as PTE, PVC, PE, PPE, or other suitable plastics, for example plastics that are heat resistant to a certain extent, bearing or carrying or supporting a plurality of spaced apart electrical conductors 25 parallel connected between two power lines 31, 33 (shown in FIG. 3) one of which is a feeder line 33 and the other is a return line 31, for example. In FIG. 1 the plurality of electrical conductors 25 are spaced equidistant with respect to each other. Each conductor 25 in FIG. 1 has a rectangular cross section. In an embodiment of the invention the plurality of electrical conductors 25 are encased in an insulating layer to provide additional safety. To simplify fabrication of the device this insulating layer can be an adhesive which attaches the plurality of electrical conductors 25 to the top and bottom isolating layers 28, 29. A power cord and plug assembly 50 is provided for powering the plurality of electrical conductors 25.

The top and bottom isolating layers 28, 29 of the electrical body stimulator 21 prevent direct contact between a user and the plurality of conductors 25 for safety reasons. In an embodiment, the top and bottom isolating layers 28, 29 are connected for forming a substantially isolating cover surrounding the plurality of electrical conductors 25 to improve safety. This isolating cover shields the plurality of electrical conductors 25 from ambient moisture.

FIG. 1 shows a cushion cover 40 surrounding the layer of pliable material 10, the electrical body stimulator 21 and the infrared reflector foil 30. Via this cushion cover 40 the device 1 becomes enclosed, for example to further isolate the device 1. Also, the cushion cover 40 can be formed of a soft and/or pliable material to increase comfort for a user, who in this manner need not directly contact the top isolating layer 28. Also, the cushion cover 40 can be used to provide an aesthetically pleasing aspect to the device 1. Additionally the cover 40 or top isolating layer 28 can be provided with therapeutic means, such as massaging protrusions. The cushion cover 40 may partially or completely surround the stack of the layer of pliable material 10, the electrical body stimulator 21 and the infrared reflector foil 30.

Figure 2:
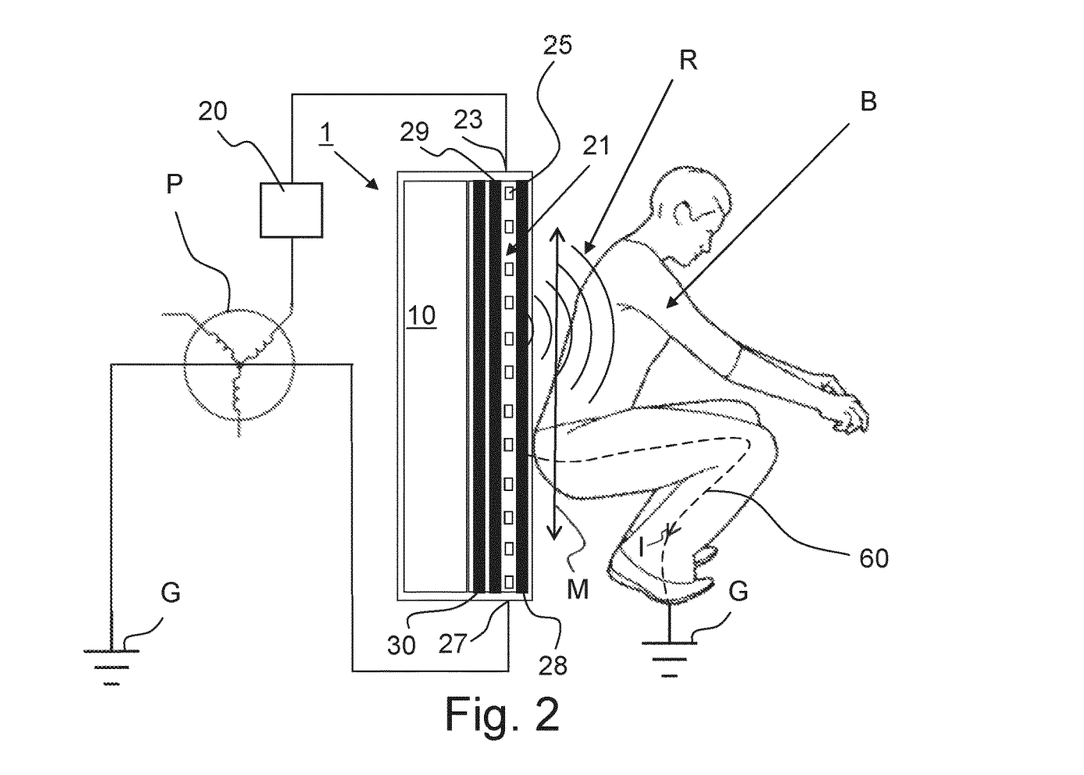
FIG. 2 shows, in a schematic form, an example of an electrical body stimulator cushion device according to the invention in use.

FIG. 2 shows, in a schematic form, an example of an electrical body stimulator cushion device 1 according to the invention in use. In FIG. 2 the electrical conductors 25 of the electrical body stimulator cushion device 1 are connected to a mains power supply P via the electrical connecting means 23, 37 and 27, 35. A body B of a user is placed in mechanical contact with the device 1 at the top isolating layer 28 side of the device 1. In FIG. 2 it can be seen that, when connected to a midpoint or neutral grounded mains power source P, such as a standard 230V AC mains, the plurality of electrical conductors 25 of the electrical body stimulator 21 firstly emit infrared radiation R in the direction of the body B. Secondly, the plurality of electrical conductors 25 generate a magnetic field M towards the body B at a distance from the electrical body stimulator cushion device 1 and thirdly, through the top isolating layer 28 and the cushion cover 40 a current pathway 60 for directing a body stimulating current I from the plurality of electrical conductors 25 via the body B to ground or earth G is provided. In use, the generated infrared radiation R, magnetic field M, and body stimulating current I stimulate, i.e. affect the body B. The electrical body stimulator cushion 1 itself also heats up due the current flowing through the plurality of electrical conductors 25. This heat is also directed towards the body B for additional stimulation thereof.

Those skilled in the art will appreciate that in the case of powering the electrical body stimulator cushion device 1 from a power source other than mains P or via an isolating transformer connected to mains, the current pathway 60 can be established by connecting one of the electrical connecting means 23, 37 or 27, 35 of the electrical body stimulator 21 to ground G, thereby creating an artificial ground connection of the power source.

The infrared reflector foil 30 reflects the infrared radiation R impinging on its surface towards the body B, thus yielding an energy efficient system. As stated above, the plurality of conductors 25 also generate heat which is, in an embodiment, prevented from diffusing away from the body B by the heat reflector foil 30 and the bottom isolating layer 29. When a person is sitting or lying on the device 1, the layer of pliable material 10 is preferably designed to be isolating to reduce the heat flow there through.

Preferably, the spacing of the plurality of conductors 25 is such that the reception of infrared radiation R, body stimulating current I, and magnetic field M in the body B are optimal. To this end, the device 1 is flexible and/or pliable to adapt to the contours of the body B in order to facilitate a better energy transfer towards the body B. The body B may be a human as well as an animal body.

FIG. 2 further shows the current pathway 60 of the body stimulating current I, which runs from the plurality of conductors 25 through the top isolating layer 28 (and the cushion cover 40, if present), to one or more points of contact of the body B and the device 1, and from there via the body B to ground G. At production of the electrical body stimulator 21, the thickness of the top isolating layer 28 can be adjusted to adjust the effective resistance along the current pathway 60 and thereby the strength of the stimulating current I.

Figure 3:
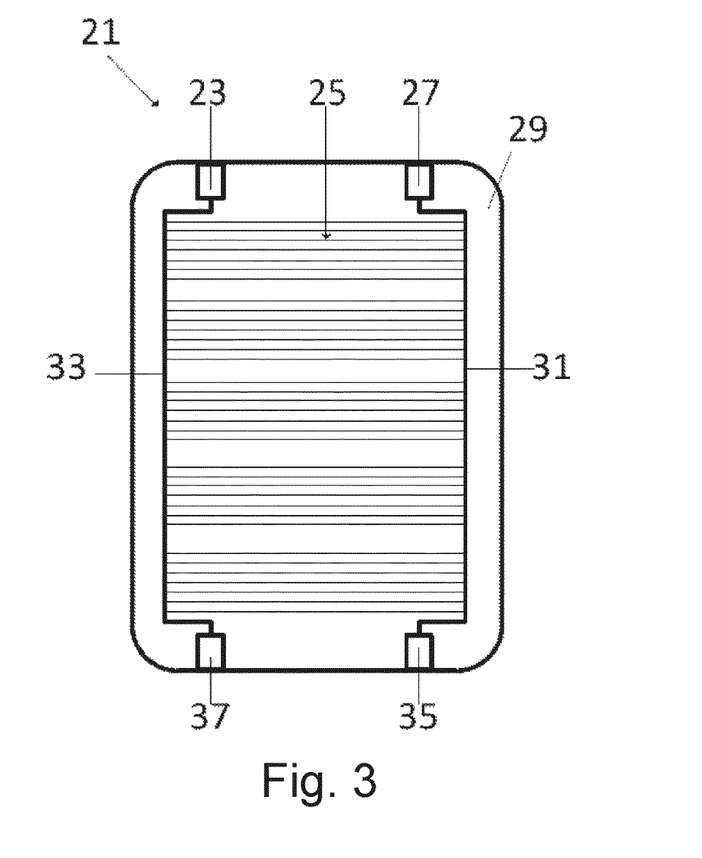
FIG. 3 shows, in a schematic form, a top view of an example of an electrical body stimulator according to the invention.

FIG. 3 shows, in a schematic form, a top view of an example of an electrical body stimulator 21 according to the invention. The plurality of spaced apart electrical conductors 25 which are parallel connected between two power lines 31, 33 one of which is a feeder line 33 and the other is a return line 31, for example.

When powered by an electric power source P, such that an electric current flows from the feeder line 33 via the conductors 25 to the return line 31, the dissipated energy by the conductors 25 and/or the power lines 31, 33 is converted to infrared radiation, IR, a magnetic field M, and a body stimulating current I.

A person skilled in the art will appreciate that the amount of radiation and the wavelength of the infrared radiation R emitted, depends on the power applied and dissipated by the electric body stimulator 21. To this end, a power control 20, such as a variable resistor or commercially available electronic power control may be arranged in the electrical connection lines of the electrical body stimulator 21 and the power source P, as schematically indicated in FIG. 2. Similarly this power control 20 may control the generated magnetic field M and body stimulating current I. Specifically the body stimulating current is determined by the effective resistance along the body stimulating pathway. This effective resistance can be modified, for example, by adjusting the thickness of the top isolating layer 28 to obtain the desired amount of body stimulating current. The electrical body stimulator 21, i.e. the electrical conductors 25 thereof, may be suitably constructed and dimensioned to operate at a wide variety of electric mains voltages and currents, for example at AC or DC voltages of 12 volts, 24 volts, 48 volts, 110 volts, 230 volts, 400 volts or even higher.

To avoid safety risks, the power control 20 may be arranged for switching off the powering of the electric body stimulator 21 in case of a too high current flow leading to an over temperature of the device and/or to avoid other hazardous safety risks for a user, such as known to a person skilled in the art.

A person skilled in the art will appreciate that the voltage drop of the lines 31, 33 in their elongated direction is directly related to the width and thickness of the power lines 31, 33. In case the device 1 is to be used in applications wherein a relative long distance is to be covered, either by the device itself or by a plurality of interconnected or cascaded devices 1, wider and/or thicker power lines 31, 33 are to be used compared to situations wherein only a relatively small distance is to be covered.

In an embodiment, the electrical body stimulator 21 is further equipped with mating electrical connecting means 23, 27, 35, 37 for electrically connecting the power lines 31, 33 of a first device 1 with power lines 31, 33 of a second device 1.

In an embodiment of the invention, in particular for adjusting the wavelength of the infrared radiation emitted by the electrical body stimulator 21, the electrical body stimulator cushion device 1 comprises an adjustable or controllable electric power control for controlling the power applied to the electrical body stimulator 21. In particular for emitting infrared radiation in the Far Infrared Region, FIR, in particular for emitting infrared radiation having a wavelength in a range of about 6000-14000 nm.

Figure 4:
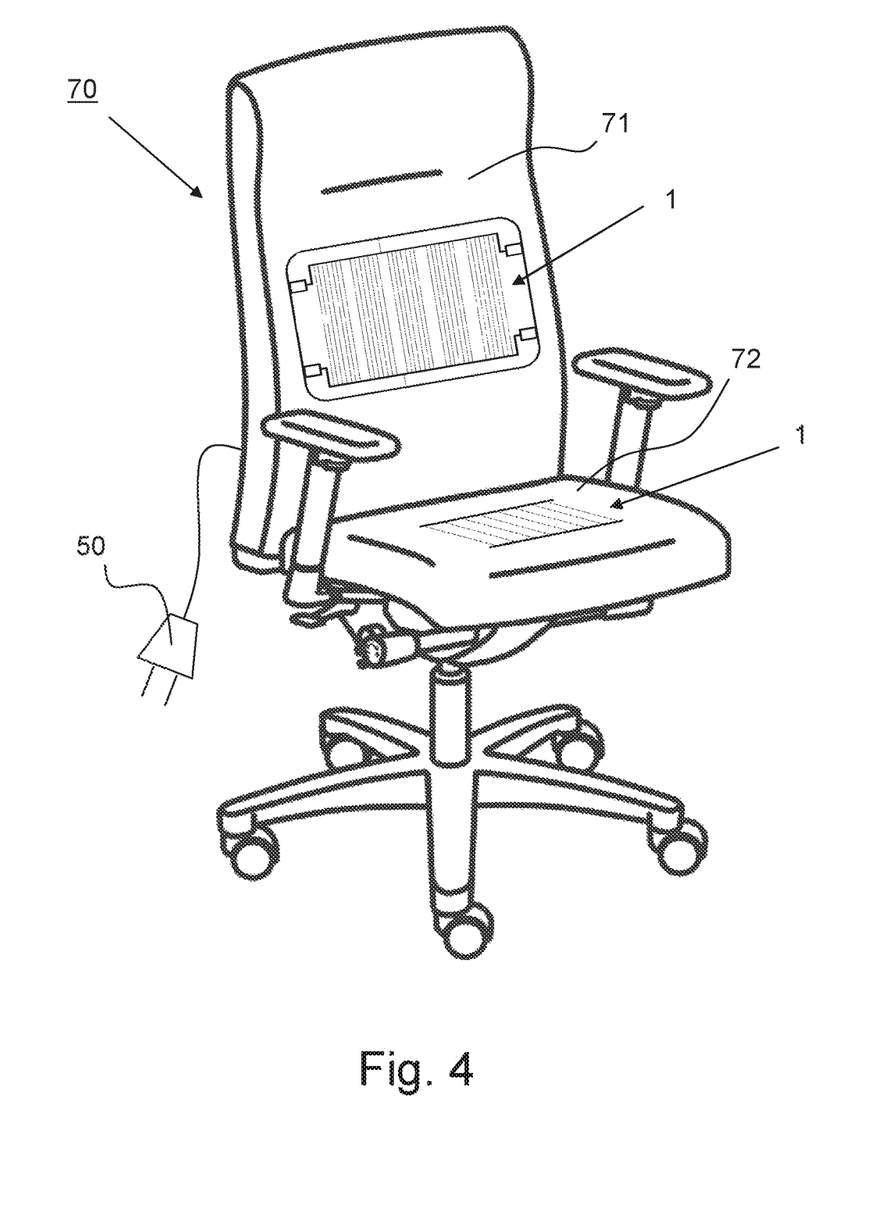
FIG. 4 shows, in a schematic form, an example of a chair comprising an electrical body stimulator cushion device according to the invention.

FIG. 4 shows, in a schematic form, an example of a therapeutic or medical treatment device in the form of a chair 70 comprising an electrical body stimulator cushion device 1 according to the invention. The chair 70 comprises a substantially vertically arranged electrical body stimulator cushion device 1 in its back support 71 and a substantially horizontal electrical body stimulator cushion device 1 in its seat support 72. Both devices 1 can be connected, for example in series, to a mains power source P via a single cord and plug assembly 50. The electrical body stimulator cushion device 1 can thus be comfortably and unobtrusively used by a user. The electrical body stimulator cushion device 1 according to the invention can also be applied in other medical or therapeutic devices, such as a medical or therapeutic bench, bed, table, matrass, bandage, or brace. In this manner the device 1 can be used in wellness therapy, natural health care, physiotherapy, thermotherapy, heat therapy, electromagnetic therapy, and/or electrotherapy.

Figure 5:
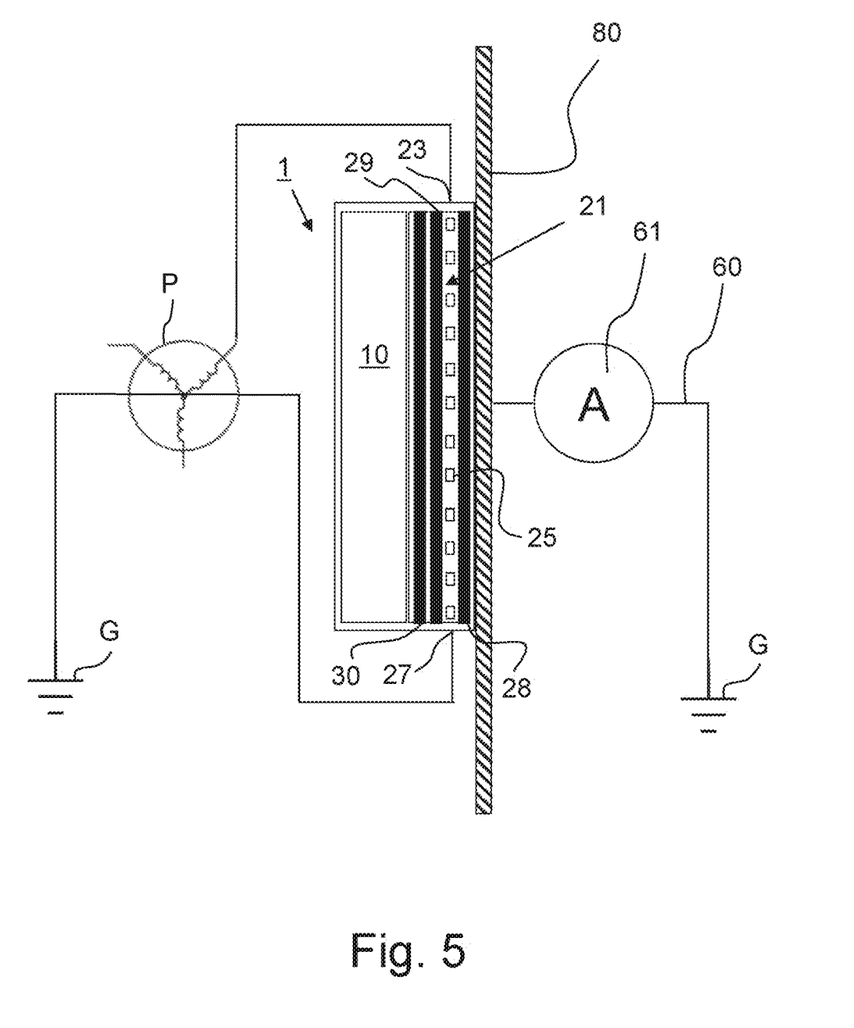
FIG. 5 shows, in a schematic form, an example of a measurement setup for determining the body stimulating current produced by an electrical body stimulator cushion device according to the invention during use.

FIG. 5 shows, in a schematic form, an example of a measurement setup for determining the maximum body stimulating current I produced by an electrical body stimulator cushion device 1 according to the invention during use. The device is connected to a mains power supply P similar to the manner described in reference to FIG. 2. The device 1 with its cushion cover 40 is placed at and in contact with a conductive plate 80, such as a metal plate. The top isolating layer 28 side of the device 1 is facing the plate 80. Optionally the cushion cover 40 can be removed to bring the plate 80 into direct contact with the top isolating layer 28. The plate 80 is connected to ground G via a current meter A 61. Thus the body stimulating current pathway 60 in FIG. 5 runs from the plurality of electrical conductors 25 though the top isolating layer 28 (and optionally the cushion cover 40) via the plate 80 through the current meter A to ground G. Compared to FIG. 2 the plate 80 and current meter A in FIG. 5 effectively replace the body B. When the device 1 is connected to the power source P, the current meter A is able to detect the amount of body stimulating current I leaking away from the device 1 through the plate 80 to ground G. This setup allows for effective determination of the maximum body stimulating current I as the current meter 61 has a negligible electrical resistance of a few milliohms, for example.

The maximum body stimulating current is determined by the configuration of the electrical body stimulator 21. In use, the effective body stimulating current is substantially determined by the effective resistance of the electrical body stimulator 21 and the body B in series. Specifically the effective electrical resistance is determined by the series connection of the electrical resistance of the top isolating layer 28, and further by the electrical resistance of any other material present between the plurality of electrical conductors 25 and the top isolating layer 28 and, if applicable, the electrical resistance of the cushion cover 40 through which the body stimulating current pathway runs when the body of the user B is in contact with the electrical body stimulator cushion device 1 and is positioned adjacent the top isolating layer 28.

The effective electrical resistance of the electrical body stimulator device 1 along the body stimulating current pathway is such that the maximum stimulating current I flowing in the body stimulating current pathway 60 as measured by the setup in FIG. 5 is always below 30 mA and preferably less than 5 mA. An effective resistance of for example, at least 46,000Ω produces a maximum current I of 5 mA when powered by a voltage of 230 V. The thickness of the top isolating layer 28 can be adjusted to achieve the desired effective resistance. In combination with the body B the total resistance along the body stimulating pathway then becomes greater, resulting in a even lower body stimulating current. This ensures an effective and passive safety mechanism.

The strength of the magnetic field M, among others, is further determined by the number of electrical conductors 25, such as the number of electrical conductors 25 per surface area of the electrical body stimulator 21. That is, the magnetic field M increases with an increase of the number of conductors 25. The magnetic field M provided towards the body B of a user may be further influenced by the material of the reflector foil 30 or by incorporating an additional foil or layer (not shown) adjacent the bottom isolating layer 29 and/or the reflector foil 30 for the purpose of directing and/or concentrating the magnetic field generated by the electrical conductors 25 towards the user body B, i.e. in the direction of the top isolating layer 28.

In a practical example of the invention, with reference to FIG. 3 above, the planar electrical body stimulator 21 is about 40 cm long and about 30 cm wide. The power line tracks 31, 33 are each about 2 cm wide whereas 31 conductor tracks 25, each being about 3 mm wide and about 30 cm long, are evenly distributed across the isolating layers 28, 29. The power consumption of this electrical body stimulator device amounts about 15-20 Watt when powered with a 230 V AC mains voltage. The maximum temperature is limited to about 80° C. and the magnetic field M produced at the isolating layer amounts about 20-30 µT.

The skilled person will appreciate that the invention has been described in the foregoing with reference to a few possible embodiments, which are preferred will stop the invention is not limited to these embodiments, however. Many modifications are conceivable within the framework of the invention. The protection being sought is defined by the appended claims.

The invention claimed is:

1. An electrical body stimulator cushion device, comprising:
   a layer of pliable material;
   a flexible electrical body stimulator comprising a plurality of interconnected electrical conductors arranged parallel to one another and a top isolating layer and a bottom isolating layer between which said plurality of electrical conductors are located;
   an infrared reflector foil, located between said layer of pliable material and said electrical body stimulator, such that said bottom isolating layer of said electrical body stimulator is facing said infrared reflector foil;
   wherein, when said electrical conductors of said electrical body stimulator cushion device are connected to a grounded power source, said electrical conductors of said electrical body stimulator, for stimulating a body adjacent said top isolating layer:
   emit infrared radiation towards said body;
   generate a magnetic field remote from said electrical body stimulator cushion device; and
   provide a current pathway for directing a body stimulating current from said electrical conductors via said body to ground, wherein said layers of said body stimulator cushion device are dimensioned to provide an effective electrical resistance of said current pathway such that a maximum body stimulating current is limited to a non-hazardous current range.

2. The electrical body stimulator cushion device according to claim 1, wherein said infrared reflector foil is an electrically isolating foil.

3. The electrical body stimulator cushion device according to claim 1, wherein said infrared reflector foil is an electrically isolating foil which is reflective for infrared radiation emitted having a wavelength in a range of 6000-14000 nm.

4. The electrical body stimulator cushion device according to claim 1, wherein said infrared reflector foil and said electrical body stimulator are arranged to direct said infrared radiation and at least one of said magnetic field and said body stimulating current towards said body to be positioned adjacent said top isolating layer.

5. The electrical body stimulator cushion device according to claim 1, wherein said effective resistance of said current pathway of said body stimulating current is such that said maximum body stimulating current is limited to a non-hazardous range of less than 5 mA.

6. The electrical body stimulator cushion device according to claim 1, wherein a thickness of said top isolating layer is adjusted to limit said body stimulating current to a non-hazardous range of less than 5 mA.

7. The electrical body stimulator cushion device according to claim 1, wherein said top isolating layer and said bottom isolating layer are connected for forming a cover surrounding said plurality of electrical conductors.

8. The electrical body stimulator cushion device according to claim 1, wherein said plurality of electrical conductors are encased in a insulating layer such that a current of no more than 5 mA is conducted to ground through a body pressed up against said insulating layer encasing said plurality of electrical conductors.

9. The electrical body stimulator cushion device according to claim 1, further comprising a cushion cover at least partially enclosing said layer of pliable material, said electrical body stimulator and said infrared reflector foil.

10. The electrical body stimulator cushion device according to claim 1, further comprising an electric power control for controlling electric power applied to said electrical body stimulator.

11. The electrical body stimulator cushion device according to claim 1, further comprising an electric power control for controlling electric power applied to said electrical body stimulator for emitting infrared radiation having a wavelength in a range of 6000-14000 nm.

12. The electrical body stimulator cushion device according to claim 1, wherein said plurality of interconnected electrical conductors form a plurality of rectangular loops.

13. The electrical body stimulator cushion device according to claim 1, wherein said body stimulator cushion device is planar and cushion-shaped.

14. The electrical body stimulator cushion device according to claim 1, wherein said body stimulator cushion device is planar and cushion-shaped, and a height of said device, measured along a stacking direction of said layers of said device, is less than a cross-section of said device, measured in a direction parallel to a plane of said layers.

15. A medical or therapeutic device, comprising at least one of a medical or therapeutic chair, bench, bed, table, mattress, and brace, in turn comprising an electrical body stimulator cushion device according to claim 1.

16. A method of using the electrical body stimulator cushion device according to claim 1 in a medical or therapeutic device, the medical or therapeutic device comprising at least one of a medical or therapeutic chair, bench, bed, table, matrass, and brace, the method comprising providing the medical or therapeutic device.

17. A method of using the electrical body stimulator cushion device according to claim 1 in at least one of wellness therapy, natural health care, physiotherapy, thermotherapy, heat therapy, electromagnetic therapy, and electrotherapy, the method comprising providing the medical or therapeutic device.

* * * * *